(12) United States Patent
Zander et al.

(10) Patent No.: US 6,261,803 B1
(45) Date of Patent: Jul. 17, 2001

(54) PROCESS FOR PREPARING FUNCTIONAL RECOMBINANT TISSUE FACTOR

(75) Inventors: Norbert Zander; Leszek Wieczorek, both of Marburg (DE)

(73) Assignee: Dade Behring Marburg, GmbH, Marburg (DE)

( * ) Notice: Subject to any disclaimer, the term of this patent is extended or adjusted under 35 U.S.C. 154(b) by 0 days.

(21) Appl. No.: 09/187,029

(22) Filed: Nov. 6, 1998

(30) Foreign Application Priority Data

Nov. 7, 1997 (DE) ............................................... 197 49 259

(51) Int. Cl.⁷ ............................ C12P 21/06; C12P 21/04; C07K 14/00

(52) U.S. Cl. ...................... 435/69.1; 435/69.1; 435/71.2; 530/350; 530/381; 530/412; 530/413; 530/416; 530/418; 530/421

(58) Field of Search ................................. 435/69.1, 69.6, 435/71.2; 530/350, 381, 412, 413, 416, 418, 421

(56) References Cited

U.S. PATENT DOCUMENTS 5,650,494 * 7/1997 Cerletti et al. ........................ 530/399

FOREIGN PATENT DOCUMENTS 0 278 776 B1    8/1988 (EP) .

OTHER PUBLICATIONS

Marston, The purification of eukaryotic polypeptides synthesized iin *Escherichia coli.* Biochem. J. 240:1–12, 1986.*
Yee et al. Recombinant Protein Expression in High Cell Density Fed–Batch Cultures of *Escherichia coli.* Bio/Technology, 10:1550–1556, Dec. 1992.*
K. von Meyenburg et al, "Physiological and Morphological Effects of Overproduction of Membrane–Bound ATP Synthase in *Escherichia Coli* K–12", Embo. J., 3(8): 1791–1797, (1984).
M.R. Maurizi, "Proteases and Protein DeGradation in *Escherichia Coli*", Experientia 48:178–201, (1992).
L.R. Paborsky et al., "Purification of Recombinant Human Tissue Factor", Biochemistry, 28(20):8072–8077, (1989).
T.S. Edgington et al., "The Structural Biology of Expression and Function of Tissue Factor", Thrombosis and Haemostasis, 66(1):67–79, (1991).
G.J. Broze et al, "Purification of Human Brain Tissue Factor", J. Biol. Chem., 260(20):10917–10920, (1985).
R. Bach et al., "Purification and Characterization of Bovine Tissue Factor" J. Biol. Chem., 256(16):8324–8331, (1981).

* cited by examiner

*Primary Examiner*—Karen Cochrane Carlson
*Assistant Examiner*—Stephen Tu
(74) *Attorney, Agent, or Firm*—Finnegan, Henderson, Farabow, Garrett and Dunner, L.L.P.

(57) ABSTRACT

The present invention relates to a process for preparing functional recombinant tissue factor in a prokaryotic host organism.

21 Claims, No Drawings

PROCESS FOR PREPARING FUNCTIONAL RECOMBINANT TISSUE FACTOR

The present invention relates to a process for preparing functional recombinant tissue factor in a prokaryotic host organism.

The contact of blood with tissue surfaces leads to a marked acceleration in coagulation. This acceleration is due to the specific effect of a factor from the tissue. This "tissue factor" is a protein which has to be associated with phospholipids in order to be able to act in a procoagulatory manner. The protein was purified for the first time from bovine brain in 1980 (Bach et al., J. Biol. Chem. 256 (16), 8324 (1981)); human tissue factor was also subsequently purified (Broze et al., J. Biol. Chem. 260 (20), 10917 (1985)). Amino acid sequences of this protein were used to design oligonucleotide probes which enabled the protein to be cloned. The primary translation product is a polypeptide composed of 295 amino acids. The surface domain, together with the receptor domain, takes up the 219 N-terminal amino acids. A transmembrane domain of 23 amino acids in length and a cytoplasmic moiety of 20 amino acids in length follow in the C-terminal direction (Edgington et al., Thromb. Haemostas. 66 (1), 67 (1991)). The solitary cysteine in the cytoplasmic domain can serve as the acceptor for a palmitate or stearate residue, which is linked by way of a thioester bond. Two intramolecular disulfide bridges are located in the extracellular domain; the C-terminal of these is required for binding factor VIIa. The surface domain is glycosylated by way of three threonine residues.

According to the currently accepted model of the initiation of coagulation, a blood vessel lesion, for example, leads to blood making contact with endothelial cells. Factor VII or factor VIIa from blood plasma binds to the tissue factor receptor on the endothelial cells. In the presence of calcium and phospholipid, factor X is converted into factor Xa by the complex on the cell surface. The factor Xa in turn converts prothrombin into thrombin, while the latter converts fibrinogen into fibrin. Finally, a local clot is formed.

The protein has been expressed in various systems using the cloned human cDNA. For example, Paborsky et al., Biochemistry 28, 8072 (1989), report its overexpression in E. coli.

The expression of eukaryotic proteins in E. coli is associated with a number of fundamental problems. One of these basic problems is that the bacteria lack their own glycosylation systems. Proteins whose functional activity depends on a glycosylation cannot be expressed in active form in E. coli. Another problem is the high activity of cell-specific proteases in E. coli (Maurizi et al., Experientia 48, 176 (1992)), which activity limits the stability of the translation products which are formed from inserted foreign genes. Finally, a fundamental problem associated with expressing tissue factor in E. coli is that this protein is a membrane protein. It is known that the rate at which membrane proteins are expressed is markedly lower than that at which soluble proteins are expressed, presumably because the uptake capacity of the cellular compartment in which the over-expressed molecules become deposited, i.e. the membranes of the bacterial cells, is limited. While it has already been reported that this uptake capacity can be increased by forming lamellar membrane structures (intracellular membrane invaginations), which are similar to those in mitochondria or chloroplasts, these structures have so far only been observed when E. coli-specific membrane proteins are being overexpressed and not in the case of heterologous eukaryotic proteins ("exclusion bodies", von Meyenburg, K. et al. EMBO Journal, Vol. 3, 1791–1797, 1984).

An alternative strategy is therefore to express a mutated tissue factor molecule which lacks the transmembrane domain. This so-called "soluble" tissue factor accumulates in the cytoplasm of the bacterial cells and can be expressed in E. coli in relatively large quantities. However, in this system, the problem can arise that the tissue factor is present in the E. coli cell in a quasicrystalline state in the form of so-called inclusion bodies. When this is the case, the inclusion bodies have to be solubilized by using very large quantities of chaotropic agents, and the proteins which have been monomerized in this way have then once again to be refolded, with a great deal of effort and usually with only a low yield, into an active, renatured confirmation.

However, in principle, the soluble tissue factor is not suitable for use in prothrombin time reagents since it lacks the domain for the interaction with phospholipids. It would only be possible to avoid these difficulties by integrating the native protein into a lipid membrane during biosynthesis of the protein. The particular advantage of the procedure would be that, on the one hand, the stability of the protein would be increased as a result of integration into the membrane and, on the other hand, this integration would also stabilize the biologically active confirmation. Another approach to overexpressing the tissue factor is that of using large number of known and successfully employed expression systems which encode products of gene fusions (e.g. with β-galactosidase, MalE, glutathione transferase and His-tag). However, these systems are not suitable for expressing biologically active tissue factor. While expression products can indeed be detected, and the level of expression can also be increased, when these systems are used, this is at the same time associated with complete loss of function, which cannot be restored, either, even using elaborate renaturation methods.

The various problems of overexpression in E. coli which have been mentioned can be circumvented by carrying out the expression in a eukaryotic system. Thus, expression in yeast, in an insect cell culture using baculovirus as a vector, or in cultured mammalian cells, for example hamster ovary cells, or in human cell lines (Paborsky et al., 1989), for example, is in principle suitable. However, these systems suffer from crucial disadvantages with regard to cost.

There is so far no known process for preparing large quantities of complete, biologically active, recombinant tissue factor from E. coli in high yield and at a high level of purity.

Strategies for purifying native and recombinant tissue factor are described in the literature, e.g. in Paborsky et al., 1989. As a rule, a detergent, for example deoxycholate or Triton-X 100, is used to extract the tissue factor from cells or tissue. The purification strategies contain a variety of chromatography processes. These extend from gel filtration via ion exchange chromatography and hydrophobic interaction chromatography through to steps involving affinity chromatography. Factor and antibodies against tissue factor are described as affinity materials (Paborsky et al., 1989). A feature common to the published purification methods is that their use is restricted to a fermenter volume of up to 1 L. There has previously been no description of a robust method for preparing relatively large quantities of pure tissue factor on a pilot plant scale (fermenter volume of 10–100 L).

Tissue factor is used in prothrombin time reagents, for example. In this case, a blood plasma sample is coagulated with an excess of tissue factor in the presence of phospholipids and calcium. That which is diagnostically relevant is the coagulation time, which can be converted, for example, into activity values in % of the standard, or into prothrombin ratio values, using suitable calibration systems. The test is used for screening the extrinsic coagulation system, for example before operations, for checking the activity of the individual factors of the extrinsic coagulation system, and for monitoring therapy in association with oral anticoagulant therapy.

Other diagnostic uses of the tissue factor are also conceivable in addition to this standard use, for example in a test for the tissue factor pathway inhibitor, in neutralization tests for lupus anticoagulants or as an amplification and detection system for immunological tests.

The possibility of using tissue factor therapeutically for treating chronic bleeding is under discussion. The hemorrhagic tendency in this connection can be congenital (hemophilia) or acquired (antibodies against coagulation factors, disturbed synthesis of coagulation factors in the liver, or disseminated intravascular coagulation). It was shown in an animal model of hemophilia that an injection of recombinant tissue factor was well tolerated and that no disseminated intravascular coagulation occurred. It was even possible for this infusion to normalize the hemostatic system for a short period (EP-A 0 278 776).

The present invention was therefore based on the object of providing a robust process for preparing relatively large quantities of pure tissue factor on a pilot plant scale (fermenter volume of 10 liters or more).

Surprisingly, it has now been found that a high expression yield of the complete tissue factor molecule can be achieved in *E. coli* by using a vector which contains a signal sequence from *Bordetella pertussis* which directs the expression product into the periplasmic space of the bacterial cell. The known standard media and standard methods for fermentation and for expression of recombinant proteins in *E. coli* were not effective. Substantial alterations in the metabolism of the host cell had to be induced so that, on the one hand, expression of thromboplastin was initiated and, on the other hand, the vitality of the host cell and the biological activity of the protein were maintained. Astonishingly, a high cell density is an essential prerequisite for successfully altering metabolism so that tissue factor is produced during culture of the recombinant *E. coli* host. Within the meaning of the invention, a high cell density is a density of at least 50 g of cells/l, preferably of 50–250 g of cells/l, very preferably of 150–200 g of cells/l. This corresponds approximately to an optical density at 650 nm, and with a pathlength of 1 cm, of 50–110. This is achieved by a high proportion of complete medium components being present during culture, with the origin of these components also being of importance. For example, while peptic or tryptic hydrolysates of animal tissues (peptone, tryptone or Luria broth) are suitable for culturing the organism and also give rise to comparable biomass yields, these media are not suitable on their own for creating the conditions for achieving an expression which is associated with satisfactory yields of protein product. It is also important that an additional complex growth-promoting substance component (yeast extract) is provided as a major constituent of the culture medium and that provision of appropriate trace elements is ensured by feeding them in separately. Surprisingly, the essential prerequisite for synthesizing the gene product, after the system has been derepressed, is that a carbon source (e.g. glucose) has to be provided at the beginning of the fermentation, thereby leading, after the source has been used up, to a dramatic change in the metabolism of the *E. coli* (carbon deficiency, diauxy effects). In parallel with this, the respiratory performance of the bacterial cells falls off, as is evident from an equally dramatic decrease in oxygen partial pressure ($PO_2$), even though the cells have to be cultured with a maximum supply of air. This on its own still does not lead to an economical biosynthesis of the tissue factor protein; a precisely defined minimum period of time in which the cells remain in a state of carbon starvation is required in addition. Synthesis of the human recombinant tissue factor can only be induced efficiently when provision of the carbon source is resumed once again following this minimum period. If this period is not adhered to, there is either no expression or the expression which does take place is lower by a factor of 10. A particularly surprising fact in this connection is that the bacterial cells have to remain in a state of carbon deficiency for this defined minimum dwell time to be able at all to continue or initiate the induction process (derepression of the repressor protein and transcription of the cloned gene). On the other hand, the carbon source (e.g. glucose) has to be added continuously in order to maintain subsequent synthesis. In addition, it was found that the stability of the product can be improved by using a protease-deficient strain of *E. coli*. After the cells have been disrupted, the tissue factor can be extracted completely using detergents. Surprisingly, a major portion of the accompanying host proteins was successfully removed by means of a PEG precipitation followed by tangential flow filtration, since PEG/protein coprecipitates normally react in a very sensitive manner to shearing forces and disintegrate once again. Low molecular weight contaminants were separated off by means of a diafiltration.

In order to be able to use the tissue factor in diagnostic or therapeutic compositions, it must be produced in a pure and concentrated form. Proteases which limit the stability of the product are a particular source of interference in diagnostic compositions. In therapeutic compositions, all foreign proteins derived from *E. coli* have the potential ability to give rise to unintended side effects. As a rule, chromatographic methods are used for purifying proteins. Examples of suitable methods are gel chromatography, hydrophobic interaction chromatography, ion exchange chromatography and affinity chromatography. When heterologous cDNAs are being over-expressed in *E. coli*, a single chromatographic step is frequently sufficient to achieve purification. The purification of tissue factor by the method described in the present document had to take into consideration three unfavorable circumstances:

1. In the first place, in its expressed form, tissue factor is a membrane protein which possesses a transmembrane domain. This protein is not soluble in the buffer systems which are routinely used for chromatographic purposes. It was found that it was also possible to carry out the requisite chromatographic steps in the presence of a detergent. Various classes of detergent are suitable for use in this context. However, preference is given to using nonionic detergents in order to rule out the possibility of ionic interactions between the detergent and ligands of the matrices employed. All nonionic detergents can be used, but preferably Triton-X 100 or octyl glycoside, particularly preferably Triton-X 100. The concentration of the detergent which is used is also of crucial importance. The critical micellar concentration of a detergent indicates the total concentration above which micelles are formed spontaneously from detergent molecules . In the case of Triton X-100, this value is between 0.01% and 0.06%, depending on the ionic strength. As far as possible, it was necessary to try to adjust to a concentration which was below the critical micellar concentration in order to prevent the formation of detergent micelles.

2. As a membrane protein, the quantity of tissue factor expressed per cell is more likely to be low. In contrast to soluble proteins, which are not infrequently produced in such a large quantity that they precipitate out in insoluble form within the cells, membrane proteins have only a limited space at their disposal even if they are channelled into the correct cell compartments. In the case of the process described in the present document, the tissue factor product represents only <1% of the protein contained in the extract obtained after extraction has taken place. More than 99% of accompanying protein has therefore to be removed.

3. The preservation of intact protein in the extract and, respectively, the intermediate stages of the purification process is also of importance. It was only possible to achieve this by including protease inhibitors in the buffers. If no protease inhibitors are added, a massive degradation of protein can be observed in fresh extracts of *E. coli* even during short dwell times. Inhibitors for different classes of proteases can be obtained commercially. It was found that the greatest success is achieved by using serine protease inhibitors. All inhibitors of serine proteases can be used; preference is given to using benzamidine and antagosan. By contrast, the use of inhibitors of members of other protease families (acid proteases or cysteine proteases) or of aminopeptidases or carboxypeptidases did not lead to any improvement in the stability of the tissue factor.

The choice of the chromatographic steps, and the sequence in which they are used, is crucial for the success of a purification strategy. It was found, surprisingly, that, despite the difficult starting position (low concentration of the product, necessity to include detergents, and interfering proteases), it was possible to purify to homogeneity in only two chromatographic steps. These were an ion exchange chromatography step and an affinity chromatography step.

In principle, anion exchanger and cation exchangers come into consideration for carrying out an ion exchange chromatography. Depending on the pK value of the proteins to be purified, and the pH to which the buffer has been adjusted, different proteins bind with different strengths to the exchange groups and can be eluted with increasing quantities of ions. Within the context of this invention, preference is given to strong cation exchange groups, such as Mono-S, or strong anion exchange groups, such as DEAE, QAE or Mono-Q. DEAE is particularly preferred as anion exchanger since the tissue factor binds at physiological pH values (approx. 8). Ion exchange groups may be bound to different carrier materials. For example, it is possible to use sepharose, agarose or cellulose. Preference was given to using crosslinked cellulose since this material exhibits very good resistance to pressure.

The preferred manner in which the ion exchange chromatography is carried out is described below, without there being any wish to exclude other possible ways of carrying out this step. Tissue factor was extracted from *E. coli* as described above and prepurified by means of PEG precipitation and diafiltration. This extract was treated with protease inhibitors and loaded onto the ion exchange column. The column which is particularly preferably used comprises a modified, crosslinked cellulose with the strong anion exchanger DEAE. The effective concentration of Triton-X 100 at this stage in the process is approx. 1%, that is far above the critical micellar concentration. Mixed micelles composed of detergent molecules, *E. coli* lipids and membrane proteins can therefore be expected to form. Surprisingly, it was found that, despite this, all the tissue factor binds to the column material. The tissue factor was eluted with increasing quantities of salt, preferably sodium salts, particularly preferably sodium chloride. The concentration which is required for complete elution is <0.1 M. As a rule, the ion exchange chromatography yield which is achieved is >80%, with the purification being approx. 3-fold.

An affinity chromatographic method was chosen as a second purification step. The eluate from the ion exchange chromatography still only contains <3% of tissue factor based on the total protein, so that it is sensible to choose a step for the ultrapurification which is as specific as possible. In principle, antibodies, dyes or physiological ligands are suitable for use as affinity ligands. Preference was given to using antibodies against tissue factor, particularly preferably monoclonal antibodies. As a rule, the affinity ligand is coupled covalently to a carrier material. Once again, agarose, sepharose or cellulose is suitable for this purpose. In the case of the invention which is described here, preference was given to using sepharose which was already preactivated. The antibody was coupled by means of epoxy chemistry. The eluate from the ion exchange chromatography was loaded onto the antibody/sepharose column. A washing step was carried out using a buffer which contained protease inhibitor and also contained Triton X-100 at a concentration which was below the critical micellar concentration. The antigen/antibody complex which forms has to be dissociated to allow elution to take place. Salts, chaotropic agents or acid, for example, can be used for this purpose. Within the context of this invention, preference was given to using a glycine buffer, particularly preferably at pH 2. The eluted tissue factor was neutralized.

Surprisingly, it was found that the tissue factor which had been purified in this way was pure by gel electrophoresis. It was no longer possible to detect impurities in any significant concentration. The tissue factor can be stored for many months in the frozen state without addition of stabilizers. After it has been concentrated, the tissue factor can be used for a variety of purposes, for example for preparing a prothrombin time reagent, as a standard for detecting tissue factor in biological samples, or else as a constituent of therapeutically active compositions for the purpose of normalizing the coagulation system in vivo.

The following examples are intended to elucidate the invention.

EXAMPLES

Example 1

Small-scale (10 L Fermentation) Preparation of the Recombinant Tissue Factor

Preliminary culture: 600 ml of Luria broth medium (LB medium) containing 50 μg of ampicillin/ml are inoculated with the transformed strain of *E. coli* and cultured at 37° C. for 16 hours in a shaking incubator. After a further 400 ml of LB medium (50 μg of ampicillin/ml) have been added, the culture is incubated once again for from 3.5 to 4.5 hours. 800 ml of this shaking flask culture are used as an inoculum for the fermenter.

10 L fermenter: 5 L of medium having the following composition: yeast extract, 324 g; tryptone, 84 g; sodium chloride, 42 g; ammonium sulfate, 8.8 g; glucose, 125 g; trace element solution, 8.4 ml (composition: 32 mM boric acid; 0.64 mM ammonium molybdate; 0.64 mM copper(II) sulfate; 2.4 mM potassium iodide; 12 mM manganese(II) sulfate; 5.56 mM zinc sulfate); mineral medium, 670 ml (composition: 27.5 mM disodium hydrogen phosphate; 10.8 mM sodium dihydrogen phosphate; 10.4 mM magnesium sulfate; 16.8 mM potassium chloride; 25 mM citric acid; 0.8 mM iron(III) sulfate) are initially introduced for the fermentation.

The medium is adjusted to 100 µg of ampicillin/ml and 1 µg of thiamine/ml. The fermenter is inoculated with 800 ml of the preliminary culture and the bacteria are propagated at 37° C. and with maximum aeration while maintaining the pH at 7.0. 7.5 hours after the fermentation has started, from 2.0 to 2.6 L of a 50% glucose solution are pumped in (100 ml/hour) until the end of the fermentation. From 19.5 to 20.5 hours after beginning the fermentation, expression of the recombinant tissue factor is initiated by adding IPTG (final concentration, from 1 to 5 mM), and the mixture is incubated for a further 5.5 to 6.5 hours. The biomass is then harvested by centrifugation. Yield, approximately 1 to 1.5 kg.

Disruption: the entire biomass is resuspended in 4 L of 20 mM tris-HCl (pH 7.5), 5 mM EDTA, 1 mM benzamidine, 0.2 mM phenylmethylsulfonyl fluoride and homogenized in a cell homogenizer (APV-Gaulin), following which the cell extract is stirred for one hour at from 0° to 8° C. after Triton X-100 has been added to a concentration of 1%. 2% polyethylene glycol 600 is then added and the mixture is stirred for a further hour; the cell lysate is then clarified by means of tangential flow microfiltration (0.2 µm filter), with from one to two disruption volumes being additionally passed through, while maintaining the retentate-side volume, in order to rinse out the cell debris (buffer: 20 mM Tris-HCl (pH 7.5), 5 mM EDTA, 1 mM benzamidine, 0.2 mM phenylmethylsulfonyl fluoride, 0.1% Triton X-100). The filtrate is concentrated down to the extract starting volume by means of tangential ultrafiltration (10,000 kd) and diafiltered with at least 5 volumes of buffer (20 mM Tris-HCl (pH 7.5), 5 mM EDTA, 1 mM benzamidine, 0.2 mM phenylmethylsulfonyl fluoride). The yield is between 16 and 50 mg of thromboplastin per liter of extract.

Example 2
Large-scale Preparation of Recombinant Tissue Factor (100 L Fermentation)

Preliminary culture: 8 L of Luri broth medium (LB medium) containing 50 µg of ampicillin/ml are inoculated with the transformed strain of E. coli and cultured at 37° C. for from 16 to 20 hours in a 10 L fermenter. 8 L of this shaking flask culture are used as the inoculum for the fermenter.

100 L fermenter: 50 L of medium containing the following components and quantities: yeast extract, 3240 g; tryptone, 840 g; sodium chloride, 420 g; ammonium sulfate, 88 g; glucose, 1250 g; trace element solution, 84 ml (composition, see above); mineral medium, 6.7 L (composition, see above) are initially introduced for the fermentation. The medium is adjusted to 100 µg of ampicillin/ml and 1 µg of thiamine/ml.

The fermenter is inoculated with 8 L of the preliminary culture and the bacteria are propagated at 37° C. and maximum aeration while maintaining the pH at 7.0. 7.5 hours after starting the fermentation, from 20 to 26 L of a 50% glucose solution are pumped in (1 L/hour) until the end of the fermentation. 19.5 to 20.5 hours after beginning the fermentation, expression of the recombinant tissue factor is initiated by adding IPTG (final concentration, from 1 to 5 mM) and the mixture is incubated for a further 5.5 to 6.5 hours. The biomass is then harvested by centrifugation. Yield, approx. 10 to 15 kg.

Disruption: the entire biomass is resuspended in 40 L of 20 mM Tris-HCl (pH 7.5), 5 mM EDTA, 1 mM benzamidine, 0.2 mM phenylmethylsulfonyl fluoride and homogenized in a cell homogenizer (APV-Gaulin); the cell extract is then stirred at from 0° to 8° C. for one hour after having added Triton X-100 to a concentration of 1%. 2% polyethylene glycol 600 is then added and the mixture is stirred for a further hour; the cell lysate is then clarified by means of tangential flow microfiltration (0.2 µm filter), with from one to two disruption volumes being additionally passed through, while adhering to the retentate-side volume, in order to rinse out the cell debris (buffer: 20 mM Tris-HCl (pH 7.5), 5 mM EDTA, 1 mM benzamidine, 0.2 mM phenylmethylsulfonyl fluoride, 0.1%. Triton X-100). The filtrate is concentrated down to the extract starting volume by means of tangential ultrafiltration (100,000 kd) and diafiltered with at least 5 volumes of buffer (20 mM Tris-HCl (pH 7.5), 5 mM EDTA, 1 mM benzamidine, 0.2 mM phenylmethylsulfonyl fluoride). Yield between 16 and 50 mg of thromboplastin per liter of extract.

Example 3
Purification of Tissue Factor by Ion Exchange Chromatography

The detergent-containing extract of the E. coli cells is diluted 1+1 with distilled water. If the conductivity is greater than 3 mS/cm, the diluted extract is further diluted with distilled water until the conductivity is less than this value. The mixture is then filtered through a Satrobran/minicandle filter (0.45 µm/0.2 µm).

The ion exchanger Cellufine-A 500 (Amicon) is supplied as a preswollen gel. A Vantage S 250 chromatography column (Amicon) is filled with a quantity which corresponds to a subsequent gel bed volume of 5 L. Prior to the run, the gel material is equilibrated with a few gel volumes of basal buffer (10 mM Tris, 1 mM benzamidine, 5 KIU of antagosan/ml, 0.1 mM EDTA, 0.1% sodium azide, 0.%  Triton-X 100, pH 8.0).

The column run is carried out automatically on an FPLC unit using automatic gradient formation and a pump speed of 5 L per hour.

The following liquids are pumped through the column in succession:

1. 10 L of diluted E. coli extract
2. 10 L of basal buffer
3. 10 L of basal buffer supplemented with 100 mM NaCl
4. 10 L of basal buffer supplemented with 200 mM NaCl
5. 10 L of basal buffer supplemented with 1 M NaCl
6. 10 L of 0.2 N NaOH, 1 M NaCl
7. 10 L of 0.2 N HCl, 1 M NaCl
8. 10 L of 0.2 M Tris, pH 8
9. 10 L of basal buffer pH, optical density at 280 nm and ionic strength are recorded throughout the entire run. The tissue factor is eluted using a stepwise gradient of increasing salt concentration. The three fractions corresponding to the buffers containing 0.1 M, 0.2 M and 1 M concentrations of NaCl are collected automatically. The column is regenerated by means of an alkali step, an acid step and then a neutralization step.

Samples are taken from all the purification steps and their content of tissue factor is examined in an ELISA. The following table shows the results from a purification run.

| Step | Vol [L] | Tissue factor [mg/L] | Tissue factor [mg] | Tissue factor [%] |
|---|---|---|---|---|
| Extract | 10 | 16.4 | 164 | 100 |
| Flow-through | 20 | <0.1 | <2 | <1 |
| 0.1 M NaCl eluate | 10 | 13.6 | 136 | 83 |
| 0.2 M NaCl eluate | 10 | 3.6 | 36 | 22 |

-continued

| Step | Vol [L] | Tissue factor [mg/L] | Tissue factor [mg] | Tissue factor [%] |
|---|---|---|---|---|
| 1 M NaCl eluate | 10 | <0.1 | <1 | <1 |
| Regenerate | 40 | 0 | 0 | 0 |

Virtually all the tissue factor is present in the eluate fraction containing 0.1 M NaCl. The yield is >80. This fraction is used for the subsequent purification in the affinity chromatography step (see following example).

Example 4
Purification of Tissue Factor by Means of Affinity Chromatography

Using standard methods in accordance with the manufacture's instructions, a monoclonal antibody against tissue factor is covalently coupled to epoxy-activated Sepharose 6B (Pharmacia) at a concentration of 1 g of antibody per 100 g of solid carrier material. The material is packed into a chromatography column and equilibrated with basal buffer (40 mM HEPES, 1 mM benzamidine, 0.1 mM EDTA, 5 KIU of antagosan/ml, 0.05% Triton-X 100, pH 7.5).

The tissue factor-containing eluate fraction from the ion exchange chromatography is loaded onto the affinity chromatography column.

The column run is carried out automatically on an FPLC unit using automatic gradient formation and a pump speed of 1 L per hour. The following liquids are pumped through the column in succession:

1. 10 L of tissue factor-containing eluate fraction from the ion exchange chromatography
2. 2 L of basal buffer
3. 1 L of elution buffer (50 mM glycine, 0.1 mM EDTA, 0.05% Triton-X 100, pH 2.0)
4. L of basal buffer
5. 1 L of N acetic acid
6. 2 L of basal buffer pH, optical density at 280 nm and ionic strength are recorded throughout the entire run. The tissue factor is eluted by a pH drop from 8.0 to 2.0. Collection of the eluate begins automatically as soon as the pH has fallen below a threshold value of 6.5 and ends after the switch-over to basal buffer has taken place and the pH has risen once again to more than 6.8.

The eluate is concentrated down to a minimum volume (approx. 40 mL) using a filter layer of 10 kDa exclusion size in a Filtron concentrating unit (Minisette). The concentrate is then filtered through a 0.2 μm pour-on filter and frozen at −70° C.

Samples are taken from all the purification steps and their content of tissue factor is examined in an ELISA. The following table shows the results from a purification run.

| Step | Vol [L] | Tissue factor [mg/L] | Tissue factor [mg] | Tissue factor [%] |
|---|---|---|---|---|
| Column application | 10 | 13.6 | 136 | 100 |
| Flow-through | 12 | <0.1 | <2 | <1 |
| Eluate | 1 | 123 | 123 | 90 |
| Concentrate | 0.04 | 2450 | 98 | 72 |
| Regenerate | 4 | <0.1 | <4 | <2 |

All the tissue factor is in the eluate or in the concentrate. The yield is >80%. Based on the total protein content, the enrichment in this step is approx. 500-fold.

Example 5
Use of Pure Tissue Factor in a Prothrombin Time Reagent

Tissue factor is expressed in *E. coli*. The cells are disrupted and extracted with detergent. Tissue factor is purified to homogeneity from the extract by means of ion exchange chromatography and affinity chromatography.

The following are mixed together for the relipidization step:
- 125 μl of 10% soybean phospholipids (Phospholipon 25 P from Nattermann) in 50 mM glycine, pH 3
- 10 μl of 20% Triton-X 100
- 50 μl of pure tissue factor (2 mg/ml)
- 15 μl of distilled water The whole is incubated, with mixing, at 15° C.–25° C. for 2 hours. The mixture is then diluted with 100 ml of reagent buffer, comprising 50 mM HEPES pH 7.5, 12 mM calcium chloride, 0.1% sodium azide and 0.5% Polygelin. The prothrombin time reagent is then ready for use.

The coagulation time of plasmas is determined as follows. 50 μl of plasma are mixed, on a Behring Fibrin Timer A, with 100 μl of prothrombin time reagent which has been prewarmed to 37° C. The time of coagulation is ascertained turbidimetrically. The following table shows some coagulation times which have been determined in this manner as compared with using a conventional prothrombin time reagent, i.e. Thromborel S supplied by Behring Diagnostics. This latter reagent is based on native tissue factor from human placenta.

| Plasma | Dilution with isotonic NaCl solution | Coagulation time using Thromborel S [s] | Coagulation time using the prothrombin time reagent in accordance with this example [s] |
|---|---|---|---|
| Lyophilized normal plasma pool | 1 + 0 | 12.1 | 11.3 |
| Lyophilized normal plasma pool | 1 + 1 | 15.5 | 16.9 |
| Lyophilized normal plasma pool | 1 + 2 | 19 | 22 |
| Lyophilized normal plasma pool | 1 + 3 | 22 | 28.4 |
| Lyophilized normal plasma pool | 1 + 4 | 24.3 | 33 |
| Lyophilized normal plasma pool | 1 + 5 | 27.5 | 38.2 |
| Lyophilized pool from patients undergoing oral anticoagulation #1 | 1 + 0 | 36.4 | 42.1 |

The coagulation times which were determined using the prothrombin time reagent which was prepared as described above are similar to the coagulation times determined using the Thromborel S. The sensitivity of the prothrombin time reagent prepared as described in the Example toward factor deficiencies is greater than the sensitivity of the reference reagent.

Example 6
Use of Pure Tissue Factor as the Standard for Detecting Tissue Factor

Tissue factor is expressed in *E. coli*. The cells are disrupted and extracted with detergent. Tissue factor is purified to homogeneity from the extract by means of ion exchange chromatography and affinity chromatography. The protein content of the pure tissue factor is determined.

In order to construct an ELISA, a test plate is coated with 1.5 µg of anti-tissue factor monoclonal antibody per reaction site. The enzyme horseradish peroxidase is covalently coupled to an anti-tissue factor polyclonal antibody.

Pure tissue factor (2 mg/ml of protein) is diluted stepwise with a dilution buffer (50 mM HEPES, 13 mM calcium chloride, 65 mM glycine, 1% Triton-X 100, 0.1% sodium azide, pH 7.5).

The following are added to each reaction site on a test plate:

50 µl of diluted tissue factor as the standard (or diluted sample where appropriate)

50 µl of sample buffer (100 mM Tris, 10 mM EDTA, 1% Triton-X 100, 0.1% sodium azide, pH 7.5)

The plate is covered with clingfilm and incubated in a water bath at 37° C. for 15–20 minutes. The plate is washed three times with 100 µl of 'Enzygnost washing solution' (Behring Diagnostics).

100 µl of the peroxidase/polyclonal antiserum conjugate are then added in each case. The plate is covered once again with clingfilm and incubated in the water bath at 37° C. for 15–20 minutes.

During this time, for each test plate, one aliquot of 'chromogen for Enzygnost' (Behring Diagnostics) is dissolved in one aliquot of 'POD buffer/substrate for Enzygnost' (Behring Diagnostics).

The plate is washed three times with 100 µl of 'washing solution for Enzygnost' (Behring Diagnostics) on each occasion.

100 µl of 'chromogen for Enzygnost' are now pipetted into each well. The plate is incubated at room temperature in the dark for 5 minutes. 100 µl of 'stop solution for Enzygnost' (Behring Diagnostics) are then pipetted into each well.

Photometric analysis at 492 nm is carried out no later than one hour after the last pipetting step.

The following table shows the results:

| Sample | Dilution | Extinction at 492 nm | Tissue factor [mg/L] |
|---|---|---|---|
| Tissue factor, 2 mg/mL | 1:1000 | 0.776 | 2.000 |
| Tissue factor, 2 mg/mL | 1:2000 | 0.676 | 1.000 |
| Tissue factor, 2 mg/mL | 1:4000 | 0.475 | 0.500 |
| Tissue factor, 2 mg/mL | 1:8000 | 0.300 | 0.250 |
| Tissue factor, 2 mg/mL | 1:16,000 | 0.203 | 0.125 |
| Tissue factor, 2 mg/mL | 1:32,000 | 0.122 | 0.063 |
| Tissue factor, 2 mg/mL | 1:64,000 | 0.069 | 0.032 |
| Placenta extract | | 0.295 | 0.250 |
| E. coli extract | 1:100 | 0.205 | 12.500 |
| Pure tissue factor (concentrate) | 1:1000 | 0.717 | 2152.000 |

The recombinant tissue factor which has been purified from *E. coli* can be used as the standard for constructing an ELISA as described above. Detection is sensitive over a range of two orders of size. The contents in samples can be determined from a plot of the values for the standard dilutions (extinction values against content in double-logarithmic form).

What is claim is:

1. A process for preparing functional recombinant tissue factor, comprising:

expressing said recombinant tissue factor in a prokaryotic host organism, wherein said host organism is at a high cell density in a fermenter;

providing a carbon source during a stationary growth phase of the host organism while providing oxygen at a maximum rate, wherein said stationary growth phase defines a start-up phase;

allowing said carbon source to be consumed during the course of said start-up phase wherein said consumption initiates the host organism into a state of carbon deficiency;

maintaining the host organism in the state of carbon deficiency for at least 1.5 hours;

expressing said functional recombinant tissue factor by supplying the host organisms subsequent to said state of carbon deficiency, continuously with a carbon source, while providing oxygen at a maximum rate; and purifying said functional recombinant tissue factor from said host organism.

2. The process as claimed in claim 1, wherein said host organism is *Escherichia coli*.

3. The process as claimed in claim 1, wherein at least one protease of said host organism is eliminated genetically.

4. The process as claimed in claim 2, wherein said tissue factor is expressed from a plasmid vector, wherein said vector contains at least one human cDNA, and wherein said at least one human cDNA encodes said tissue factor.

5. The process as claimed in claim 4, wherein said plasmid vector contains an inducible or derepressible promoter or a specific signal sequence, wherein said promoter or signal sequence results in transporting said tissue factor into a primary cell compartment.

6. The process as claimed in claim 2, further comprising a medium for culturing *E. coli*, wherein said medium comprises yeast extract, tryptone extract, NaCl, malt extract, and buffer salts.

7. The process as claimed in claim 5, further comprising disrupting the bacteria by homogenization in a buffer containing a protease inhibitor, and incubating in the presence of a detergent to form a detergent-containing extract.

8. The process as claimed in claim 7, further comprising optionally treating the detergent-containing extract with polyethylene glycol at a concentration of from 0 to 40% with respect to the polyethylene glycol, and optionally incubating at about from 0 to 25°, for about from 0 to 6 hours, and clarifying by filtration, thereby forming a clarified filtrate.

9. The process as claimed in claim 8, further comprising processing the clarified filtrate by means of diafiltration through membranes having a molecular weight exclusion size of from 5000 to 50,000 daltons.

10. The process as claimed in claim 9, further comprising purifying the functional recombinant tissue factor from the diafiltration retentate.

11. The process as claimed in claim 10, further comprising a multi-step chromatographic purification process.

12. The process as claimed in claim 11, wherein at least one of the chromatographic steps is an ion exchange chromatography step on a cation exchanger or an anion exchanger.

13. The process as claimed in claim 12, wherein said anion exchanger is a strong anion exchange group coupled to a pressure-resistant carrier material, and further comprising eluting with a buffer.

14. The process as claimed in claim 15, further comprising an affinity chromatographic step.

15. The process as claimed in claim 14, wherein the affinity ligand is at least one of an antibody against tissue factor, and a physiological ligand of tissue factor.

16. The process as claimed in claim 15, wherein said antibody is a polyclonal or monoclonal antibody against tissue factor, and said antibody is covalently coupled to a pressure-resistant column material.

17. The process as claimed in claim 16, further comprising removing the functional recombinant tissue factor from the affinity ligand by salt, buffer having a defined pH value, or chaotropic agents.

18. The process as claimed in claim 11, further comprising concentrating the functional recombinant tissue factor to a concentration of greater than 1 g/l using a diafiltration method.

19. The tissue factor produced by the method as claimed in claim 18.

20. The process as claimed in claim 17, wherein said buffer is a dilute glycine buffer having an acid pH.

21. The process as claimed in claim 20 wherein said glycine buffer is about 50 mM glycine at about pH 2.

* * * * *

UNITED STATES PATENT AND TRADEMARK OFFICE
CERTIFICATE OF CORRECTION

PATENT NO. : 6,261,803 B1 Page 1 of 1
DATED : July 17, 2001
INVENTOR(S) : Norbert Zander et al.

It is certified that error appears in the above-identified patent and that said Letters Patent is hereby corrected as shown below:

Column 12,
Line 14, "start-up phase" should read -- start-up phase, --.
Line 21, "organisms" should read -- organism, --.

Column 13,
Line 3, "claim 15" should read -- claim 13 --.

Column 14,
Line 10, "claim 20" should read -- claim 20, --.

Signed and Sealed this

Sixteenth Day of July, 2002

Attest:

JAMES E. ROGAN
Attesting Officer *Director of the United States Patent and Trademark Office*